US00PP10206P

United States Patent [19]

Noodelijk

[11] Patent Number: Plant 10,206

[45] Date of Patent: Jan. 20, 1998

[54] CHRYSANTHEMUM PLANT NAMED 'YELLOW REMIX'

[75] Inventor: Robert Noodelijk, Woubrugge, Netherlands

[73] Assignee: Chrysanthemum Breeders Association, N.V., Netherlands

[21] Appl. No.: 739,453

[22] Filed: Oct. 29, 1996

[51] Int. Cl.[6] ..... A01H 5/00

[52] U.S. Cl. ..... Plt./74.1

[58] Field of Search ..... Plt./74.1

*Primary Examiner*—Howard J. Locker

*Attorney, Agent, or Firm*—Parkhurst, Wendel & Burr, LLP

[57] ABSTRACT

A new and distinct cultivar of Chrysanthemum plant named 'Yellow Remix', bearing medium to large sized yellow and red blooms with a green center and performance of 19-22 days.

2 Drawing Sheets

BACKGROUND OF THE INVENTION

The present invention comprises a new and distinct cultivar of chrysanthemum plant which is a natural occurring sport of a parent chrysanthemum named 'Remix', Parent Chrysanthemum 'Remix'is described in a co-pending U.S. Plant patent application Ser. No. 08/738,600. The new cultivar was discovered as a whole plant mutation in 1990 in a greenhouse in Holland.

The invention has been asexually reproduced by cuttings at the same location. The new cultivar has been found to retain all of its distinctive characteristics through successive asexual propagations.

SUMMARY OF THE INVENTION

The present invention is a new and distinct variety of Chrysanthemum of a medium to large sized bloom and yellow and red color.

BRIEF DESCRIPTION OF THE DRAWINGS

The present invention of a new and distinct variety of Chrysanthemum is shown in the accompanying drawings, the color being as nearly true as possible with color photographs of this type.

DESCRIPTION OF THE INVENTION

Figure 1:
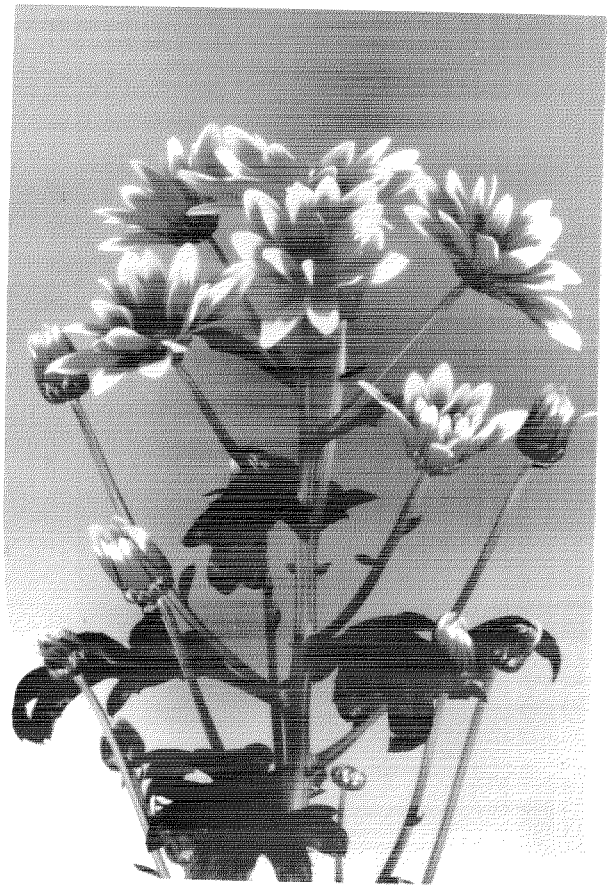
FIG. 1 shows the full bloom of the new cultivar.
Figure 2:
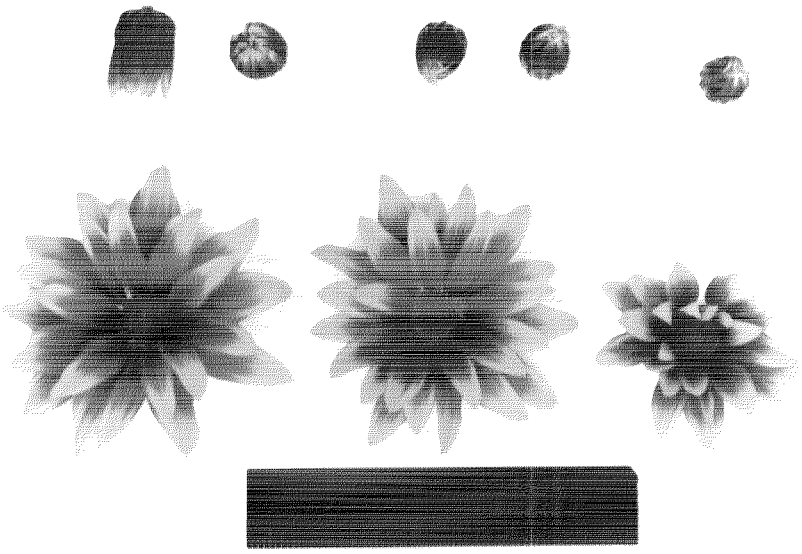
FIG. 2 shows the various states of bloom of the new cultivar.
Figure 3:
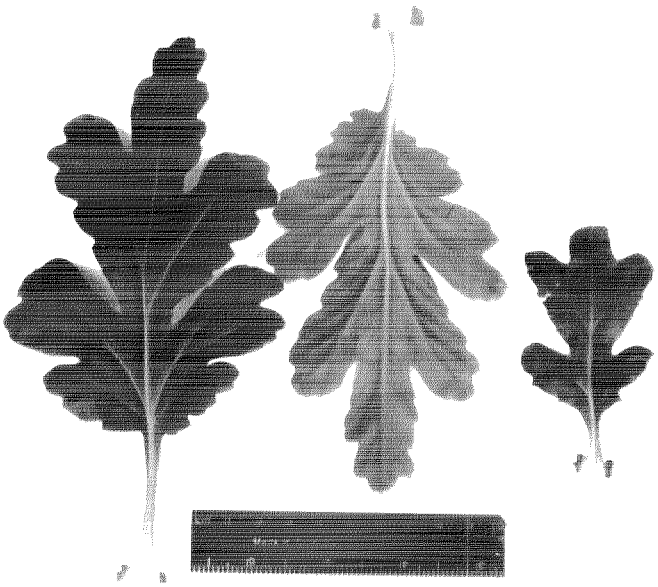
FIG. 3 shows foliage and petiole of the new cultivar.

This new variety of Chrysanthemum is of the botanical classification Chrysanthemum morifolium. When grown in the vicinity of Ter Aar, Holland, it has a response time of approximately 8 weeks. This new variety produces medium to large sized yellow and red blooms with a green center having a 3 week performance (i.e., vase life of 19–22 days). This new variety of chrysanthemum has been found to retain its distinctive characteristics throughout successive propagations and may be planted under greenhouse conditions in Holland between weeks 2 and 32. The following is a description of the plant and characteristics (color designations are from R.H.S. Color Chart) that distinguish it from related known varieties and its antecedents. The color designations are taken from the plant itself. Accordingly, any discrepancies between the color designations and the colors depicted in the photographs are due to photographic tolerances.

A comparison and botanical description of 'Yellow Remix' and related cultivar 'Remix' follows.

Botanical Classification

| CULTIVAR | YELLOW REMIX | PARENT CULTIVAR REMIX |
|---|---|---|
| Bud | | |
| Size | large cross section ±1.3 cm large height ±1.0 cm | large cross section ±1.3 cm height ±1.0 cm |
| Form | round and flat | round and flat |
| Outside Color | Greyed-Purple 187B tipped with yellow | Red-Purple 61A |
| Bloom | | |
| Size Fully Expanded | Medium to large 7–7½ cm | Medium to large 7–7½ cm |
| Borne | Upper portion single flower per peduncle, lower portion plural flower per peduncle. | Upper portion single flower per peduncle, lower portion plural flower per peduncle. |
| Peduncle Lengths | Near the top ±8 cm Near the middle ±15 cm Near the bottom ±20 cm | Near the top ±8 cm Near the middle ±15 cm Near the bottom ±20 cm |
| Peduncle Lateral Shoot, Attachment | Medium | Medium |
| Peduncle Lateral Shoot, Angle | Medium | Large |
| Form | Single (daisy) | Single (daisy) |
| Performance | Good 19–22 days (18–20° c.) | Good 19–22 days (18–20° C.) |
| Color | | |
| Center of Flower | Immature: Yellow-Green 144A Mature: Yellow-Green 144B | Immature: Yellow-Green 144A Mature: Yellow-Green 144B |
| Base of Ray florets | Red 46A | Red-Purple 72B becoming White 155D at the tips. |
| Outer Ray florets | Red 46A becoming Yellow 6A at the tips | Red-Purple 72B becoming White 155D at the tips. |
| Inside of Ray florets | Red 46A becoming Yellow 6A at the tips | Red-Purple 72B White 155D at the tips. |
| Reverse of Ray florets | Yellow 6A with strong purple tints, near Red-Purple | White 155D strongly tinged with Red-Purple 72A, |

-continued

| CULTIVAR | Botanical Classification YELLOW REMIX | PARENT CULTIVAR REMIX |
|---|---|---|
| | 59B, except at the tip. | becoming whiter at the tips. |
| Tonality from Distance | A yellow and red daisy with a green center having some pollen | A purple and white daisy with a green center having some pollen |
| Discoloration | to Red 45A becoming Yellow 6A at the tips | to Red-Purple 71D becoming White 155D at the tips. |
| Pollen | Yellow-Orange 14A | Yellow-Orange 14A |
| Ray florets | | |
| Texture | Upperside smooth, underside smooth. | Upperside smooth, underside smooth. |
| Number | 20–26 (two rows) | 20–26 (two rows) |
| Cross-section | flat; two keels | flat (no keels) |
| Arrangement | Imbricated | Imbricated |
| Persistence | Good, ray florets keep straight or reflex somewhat at the edge at the end of blooming. | Good, ray florets keep straight or reflex somewhat at the edge at the end of blooming. |
| Fragrance | Typical chrysanthemum | Typical chrysanthemum |
| Disc Diameter | Medium (±1.5 cm) | Medium (±1.5 cm) |
| Reproductive Organs | | |
| Stamen | Yellow, thick ±4 mm in length | Yellow, thick ±4 mm in length |
| Pollen | Appears fairly soon | Appears fairly soon |
| Styles | green, thick | green, thick |
| Style Length | ±6 mm | ±6 mm |
| Stigmas | yellow | yellow |
| Stigma Width | ±2 mm | ±2 mm |
| Ovaries | Enclosed in calyx | Enclosed in calyx |
| Plant | | |
| Form | Spray mum meant | Spray mum meant |

-continued

| CULTIVAR | Botanical Classification YELLOW REMIX | PARENT CULTIVAR REMIX |
|---|---|---|
| | for erect culture. Herbaceous. | for erect culture. Herbaceous. |
| Growth | Short to medium | Short to medium |
| Height | 100–125 cm | 100–125 cm |
| Stem Color | Yelow-Green 144A | Yellow-Green 144A |
| Stem Strength | Weak to medium | Weak to medium |
| Stem Brittleness | Absent | Absent |
| Stem Anthocyanin Coloration | Present | Present |
| Internodes | 2–2½ cm | 2–2½ cm |
| Flowering Response | 8 weeks | 8 weeks |
| Foliage | | |
| Color | Green 137A | Green 137A |
| Size | Length ±13 cm. Width ±9 cm. | Length ±13 cm. Width ±10 cm. |
| Quantity | 20–26 | 20–26 |
| Shape | lobed, see photograph | lobed, see photograph |
| Texture | Upperside rough, underside smooth, slightly hirsute. | Upperside rough, underside smooth, slightly hirsute. |
| Ribs and Veins | Ribs well developed, veins not so developed | Ribs well developed, veins not so developed |
| Edge | Crenated | Crenated |
| Shape of Base of Sinus Between Lateral Lobes | Round | Round |
| Margin of Sinus Between Lateral Lobes | Converging | Converging |
| Shape of Base | Truncate | Truncate |
| Apex | Mucronate | Mucronate |

I claim:

1. A new and distinct variety of Chrysanthemum plant as described and illustrated.

* * * * *